(12) United States Patent
Meyer et al.

(10) Patent No.: US 6,340,441 B1
(45) Date of Patent: *Jan. 22, 2002

(54) MULTI-LAYER GUIDE WIRE AND METHOD OF MANUFACTURE THEREFOR

(75) Inventors: Jon A. Meyer, Bellingham; Maura Rooney, Cambridge; Richard J. Quigley, Boston; Thomas F. Mirarchi, Shrewsbury, all of MA (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/042,292

(22) Filed: Mar. 13, 1998

(51) Int. Cl.[7] .................. A61M 25/00; B29C 47/06
(52) U.S. Cl. .................. 264/173.12; 264/173.16; 156/244.12; 600/585
(58) Field of Search .............. 156/244.12, 500; 264/171.14, 171.17, 173.12, 173.16; 600/585

(56) References Cited

U.S. PATENT DOCUMENTS

| | | | | |
|---|---|---|---|---|
| 3,769,085 A | * | 10/1973 | Matsubara | 264/171.17 X |
| 4,250,072 A | * | 2/1981 | Flynn | 524/288 |
| 4,282,876 A | | 8/1981 | Flynn | 128/349 R |
| 4,345,602 A | | 8/1982 | Yoshimura et al. | 128/349 R |

(List continued on next page.)

FOREIGN PATENT DOCUMENTS

| | | |
|---|---|---|
| EP | 0 340 304 A1 | 11/1989 |
| EP | 0 380 102 A1 | 8/1990 |
| EP | 0 395 098 A1 | 10/1990 |
| EP | 0 405 823 A2 | 1/1991 |
| EP | 0 407 965 A1 | 1/1991 |
| EP | 407 965 A1 * | 1/1991 .......... A61M/25/00 |
| FR | 2 401 668 | 8/1977 |
| JP | 60-12069 | 1/1985 |
| JP | 2-180277 | 7/1990 |
| JP | 8-257133 | 10/1996 |
| JP | 8-257136 | 10/1996 |
| WO | WO 85/01444 | 4/1985 |
| WO | WO 89/09626 | 10/1989 |
| WO | WO 91/00051 | 1/1991 |

OTHER PUBLICATIONS

Tegtmeyer, "Current Problems in Diagnostic Radiology", vol. XVI, No. 2, Mar./Apr., 1987, pp. 79–80.

*Primary Examiner*—Steven D. Maki
*Assistant Examiner*—Barbara J. Musser
(74) *Attorney, Agent, or Firm*—Crompton, Seager & Tufte LLC

(57) ABSTRACT

A multi-layered guide wire that uses separate layers to achieve desired guide wire characteristics. Each of the layers may enhance one or more of the desired guide wire characteristics, with the combination of layers providing the desired combination of guide wire characteristics. Each of the layers may be provided over the entire guide wire, or only over selected portions of the guide wire. Further, selected layers may be co-extruded over the guide wire, which may reduce the manufacturing costs associated therewith.

7 Claims, 2 Drawing Sheets

U.S. PATENT DOCUMENTS

| | | | | |
|---|---|---|---|---|
| 4,456,017 A | | 6/1984 | Miles | 128/772 |
| 4,483,808 A | * | 11/1984 | Dillow et al. | 264/171.17 X |
| 4,534,363 A | | 8/1985 | Gold | 128/772 |
| 4,642,267 A | | 2/1987 | Creasy et al. | 428/413 |
| 4,682,607 A | | 7/1987 | Vaillancourt et al. | 128/772 |
| 4,721,117 A | | 1/1988 | Mar et al. | 128/772 |
| 4,729,914 A | | 3/1988 | Kliment et al. | 428/36 |
| 4,739,768 A | | 4/1988 | Engelson | 128/658 |
| 4,811,743 A | | 3/1989 | Stevens | 128/772 |
| 4,835,003 A | | 5/1989 | Becker et al. | 427/2 |
| 4,841,976 A | | 6/1989 | Packard et al. | 128/657 |
| 4,867,174 A | * | 9/1989 | Skribiski | 600/585 |
| 4,884,579 A | | 12/1989 | Engelson | 128/772 |
| 4,899,787 A | | 2/1990 | Ouchi et al. | 138/131 |
| 4,922,924 A | | 5/1990 | Gambale et al. | 128/772 |
| 4,925,445 A | | 5/1990 | Sakamoto et al. | 604/95 |
| 4,955,862 A | | 9/1990 | Sepetka | 604/164 |
| 4,961,731 A | | 10/1990 | Bodicky et al. | 604/264 |
| 4,977,901 A | | 12/1990 | Ofstead | 128/772 |
| 4,991,602 A | | 2/1991 | Amplatz et al. | 128/772 |
| 5,045,072 A | | 9/1991 | Castillo et al. | 604/280 |
| 5,061,254 A | | 10/1991 | Karakelle et al. | 604/265 |
| 5,069,226 A | | 12/1991 | Yamauchi et al. | 128/772 |
| 5,078,702 A | | 1/1992 | Pomeranz | 604/280 |
| 5,095,915 A | * | 3/1992 | Engelson | 600/585 |
| 5,129,890 A | | 7/1992 | Bates et al. | 604/281 |
| 5,176,149 A | | 1/1993 | Grenouillet | 128/772 |
| 5,217,026 A | | 6/1993 | Stoy et al. | 128/772 |
| 5,333,620 A | * | 8/1994 | Moutafis et al. | 600/585 |
| 5,342,383 A | | 8/1994 | Thomas | 606/190 |
| 5,365,943 A | | 11/1994 | Jansen | 128/772 |
| 5,368,048 A | | 11/1994 | Stoy et al. | 128/772 |
| 5,409,015 A | | 4/1995 | Palermo | 128/772 |
| 5,411,476 A | | 5/1995 | Abrams et al. | 604/95 |
| 5,421,349 A | | 6/1995 | Rodriguez et al. | 128/772 |
| 5,452,726 A | | 9/1995 | Burmeister et al. | 128/772 |
| 5,507,301 A | | 4/1996 | Wasicek et al. | 128/772 |
| 5,533,985 A | | 7/1996 | Wang | 604/264 |
| 5,637,089 A | | 6/1997 | Abrams et al. | 604/95 |
| 5,680,873 A | * | 10/1997 | Berg et al. | 128/772 |
| 5,681,514 A | * | 10/1997 | Woody | 264/173.12 X |
| 5,716,574 A | * | 2/1998 | Kawasaki | 264/171.17 |
| 5,722,424 A | * | 3/1998 | Engelson | 600/585 |
| 6,093,157 A | * | 7/2000 | Chandrasekaran | 606/159 |

* cited by examiner

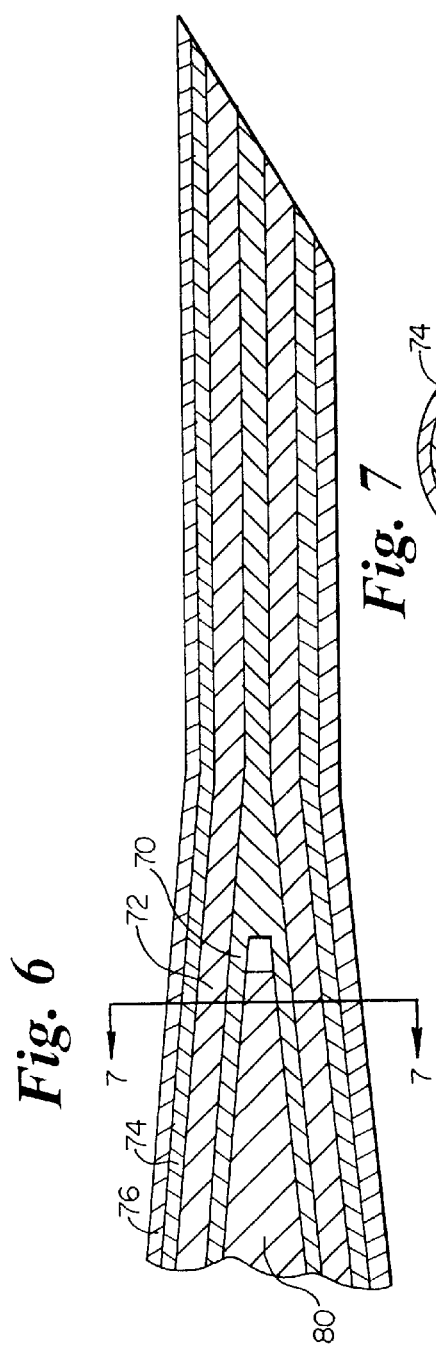
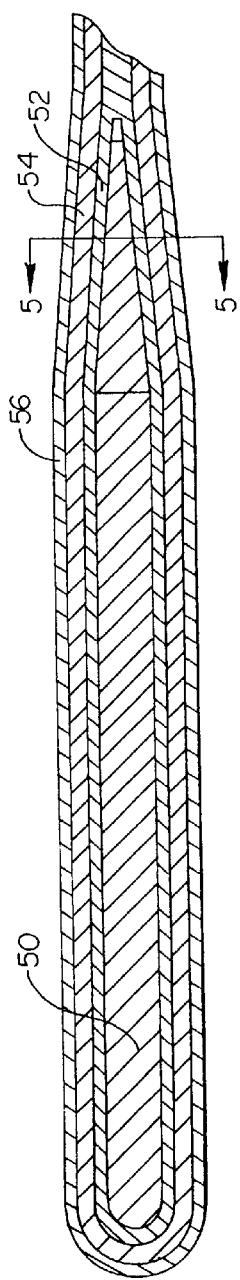
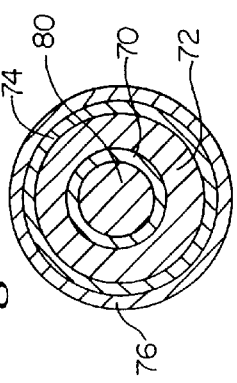
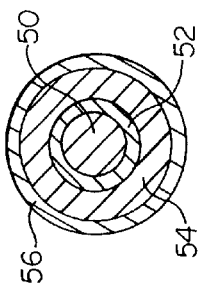
Fig. 4
Fig. 5
Fig. 6
Fig. 7

MULTI-LAYER GUIDE WIRE AND METHOD OF MANUFACTURE THEREFOR

BACKGROUND OF THE INVENTION

The present invention relates to intravascular, gastrointestinal, or urological guide wires, and methods of manufacture therefor. In particular, the present invention relates to multi-layered intravascular guide wires, and methods of manufacture therefor.

Guide wires are used in various procedures in both the coronary regions and the peripheral regions of the body. Various sizes and lengths of guide wires are made to be suitable for various uses and locations in the body. For example, guide wires of very small diameters, on the order of 0.010 to 0.018 inches, may be suitable for use in narrow coronary vessels. Such guide wires may have an extremely floppy distal tip which may be bent or preformed by the physician to facilitate placement of the guide wire at the desired location. Other guide wires have a larger diameter, for example 0.035 inches, and preformed tip. These larger diameter guide wires may be especially useful in peripheral or gastrointestinal regions of the body. Larger diameter guide wires may be provided with very flexible tips or with relatively rigid tips depending upon the particular needs of the patient and the preferences of the physician. Guide wires come in a range of sizes in addition to those discussed above.

Some of the preferred characteristics in a guide wire include support, the ability to provide a track for a balloon or other device to advance over, and good torsional transmittance. A discussion of these and other preferred characteristics of guide wires can be found in *Endovascular Surgery*, by Moore, W. S. and Ahn, S. S.; p. 157, W. B. Saunders Co. (1989). Other characteristics that are often desirable include flexibility, strength, radiopacity, color, lubricity, etc.

In many cases, providing a desired combination of guide wire characteristics can be a significant engineering challenge. In some cases, the approach used to enhance one guide wire characteristic may adversely affect another. For example, suppose a guide wire includes a plastic jacket around the distal tip of a guide wire core for support. The radiopacity of the guide wire tip may be enhanced by loading the plastic jacket with a high concentration of a radiopaque agent. However, by providing a high concentration of a radiopaque agent, the tensile strength of the plastic jacket is typically reduced. Thus, the strength of the distal tip of the guide wire is reduced, and the flexibility may be unduly reduced. This illustrates the often difficult balance between competing characteristics of a typical guide wire design.

SUMMARY OF THE INVENTION

The present invention provides a multi-layered guide wire that uses separate layers to achieve desired guide wire characteristics. Each of the layers may enhance one or more desired guide wire characteristics, with the combination of layers providing the desired combination of guide wire characteristics. Each of the layers may be provided over the entire guide wire, or only over selected portions of the guide wire. Further, selected layers may be co-extruded over the guide wire, which may reduce the manufacturing costs associated with the multi-layer guide wire design.

In one illustrative embodiment of the present invention, a guide wire is provided that includes an elongated core with an outer axial surface. At least two outer jacket layers are co-extruded over at least a portion of the outer axial surface of the elongated core, and preferably over only the distal portion thereof. Each of the at least two outer jacket layers preferably have at least one physical property that differs from another one of the outer jacket layers. Illustrative physical properties include flexibility, radiopacity, strength, color, bonding characteristics, lubricity, etc.

In another illustrative embodiment of the present invention, a first and a second outer jacket layer are co-extruded over the distal end of the elongated core. The first outer jacket layer, which is disposed closest to the elongated core, may include a plastic that is loaded with a relatively high concentration of a radiopaque agent, such as tungsten, tantalum, platinum, gold, etc. This enhances the radiographic signature of the distal end of the guide wire. As indicated above, however, loading the first outer plastic jacket layer with a relatively high concentration of a radiopaque agent typically reduces the tensile strength thereof. To compensate for the reduced strength, the second outer jacket layer, which preferably has little or no radiopaque agent therein, is provided over the first outer plastic jacket. The combination of the first and second outer jacket layers provides a guide wire that has a highly radiopaque distal tip, and yet retains the desired strength characteristic.

In another illustrative embodiment, a first and a second outer jacket layer are co-extruded over selected portions of the elongated core. The term "selected portions" includes the entire elongated core, various sections of the elongated core, the distal tip of the core, etc. In this embodiment, the first outer jacket layer, which is disposed between the elongated core and the second outer jacket layer, is formed from a bonding material that is particularly suited for forming a bond between the second outer jacket layer and the elongated core. This provides an efficient method for bonding a plastic jacket to an elongated core, and in particular a metallic elongated core, without having to apply an adhesive or the like to the elongated core by conventional methods such as dipping or spraying. It has been found that this may reduce the cost of producing a guide wire that has one or more plastic jacket layers thereon.

It is contemplated that the bonding layer may be co-extruded with any number of layers. For example, a guide wire may be formed by co-extruding a bonding layer, an inner plastic jacket and an outer plastic jacket over at least a portion of an elongated core. The inner plastic jacket may, for example, have a first concentration of a radiopaque agent, and the outer plastic jacket may have a second concentration of a radiopaque agent. The bonding layer preferably forms a bond between the elongated core and the inner plastic jacket. A lubricious layer may be co-extruded along with the bonding layer, the inner plastic jacket and the outer plastic jacket to provide a lubricous outer surface thereto.

Finally, and in another illustrative embodiment of the present invention, a number of outer jacket layers are co-extruded over a mandrel or the like to produce a multi-layer tip assembly having a lumen. In one embodiment, the distal end of a guide wire is positioned in the lumen and the tip assembly is heated. By selecting the appropriate materials, the multi-layer tip assembly may shrink as a result of the heating process, securing the tip to the distal end of the guide wire. In another embodiment, a bonding adhesive may be used, wherein the bonding adhesive may be pressure activated or heat activated. Thus, the tip assembly may be secured to the distal tip of the guide wire by simply applying pressure or heat as appropriate.

BRIEF DESCRIPTION OF THE DRAWINGS

FIG. 4 is a cross-sectional side view of another embodiment of the present invention;

FIG. 5 is a cross-sectional view of the embodiment of FIG. 4 taken along line 5—5;

FIG. 6 is a partial cross-sectional side view of a distal portion of yet another embodiment of the present invention; and FIG. 7 is a cross-sectional view of the embodiment of FIG. 6 taken along line 7—7.

DETAILED DESCRIPTION OF THE PREFERRED EMBODIMENTS

Figure 1:
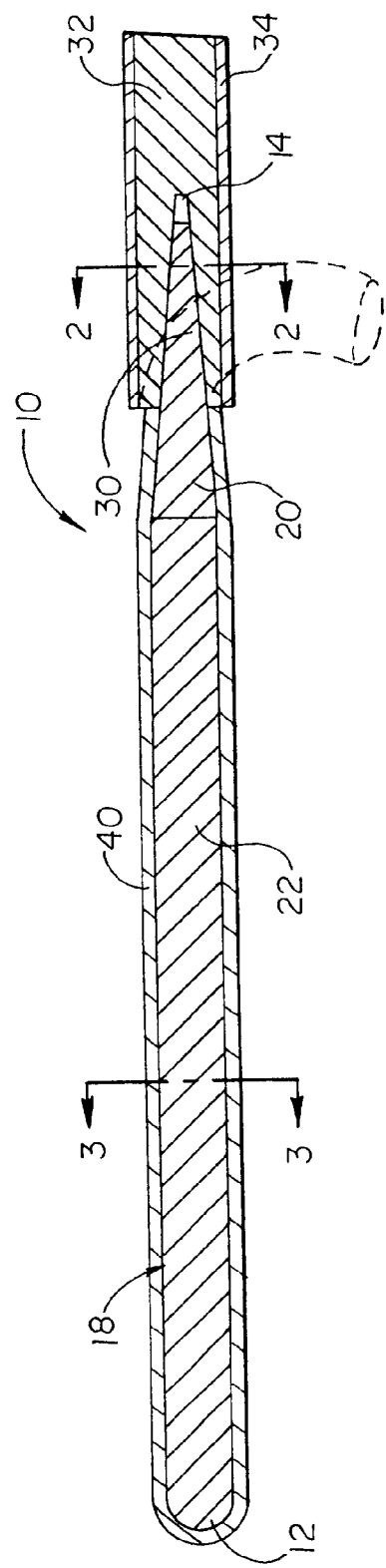
FIG. 1 is a cross-sectional side view of a first embodiment of the present invention.

Referring to FIG. 1, there is depicted a first illustrative embodiment of the present invention. This embodiment is an intravascular guide wire 10. The guide wire 10 is typically about 150–450 centimeters in length and has a typical outside diameter of approximately 0.035 inches. Other lengths and diameters may be provided so that a range of sizes of guide wires may be available suitable for the different needs of various individual patients and the preferences of physicians. Such other sizes are contemplated to be within the scope of the present invention and of this embodiment in particular.

The guide wire 10 includes a core wire 18 having a proximal end 12 and a distal end 14. The core wire may be made of a strong, yet flexible material, such as a metal like stainless steel, Nitinol, titanium, MP35N, ELGILOY®, or other materials, or combinations thereof. The distal end 14 may be shaped to provide a J-tip or other desired bend configuration. The J-tip configuration is shown in phantom lines 38.

In a preferred embodiment, the core wire 18 includes a distal portion 20 and a proximal portion 22. The proximal and distal portions are preferably formed of a single metallic wire. The distal portion 20 has a smaller cross section than the proximal portion 22 to impart greater flexibility to the distal end of the guide wire 10. In a preferred embodiment, the distal portion 20 of the guide wire is tapered to impart increasing levels of flexibility to the guide wire toward the distal end 14. The tapered distal portion 20 preferably has a length of about 20 centimeters.

In the illustrative embodiment, the distal portion 20 has a distal tip portion 30. At least two outer jacket layers 32 and 34 are co-extruded over at least a portion of the distal tip portion 30, as shown. Each of the at least two outer jacket layers preferably has at least one physical property that differs from another one of the outer jacket layers. Illustrative physical properties include flexibility, radiopacity, strength, color, bonding characteristics, lubricity, etc.

In one illustrative embodiment, the first outer jacket layer 32, which is disposed closest to the elongated core wire 18, includes a PEBAX material that is loaded with a relatively high concentration of a radiopaque agent, such as at least about 50 percent by weight of tungsten, tantalum, platinum, or gold, and preferably 80 percent. This enhances the radiographic signature of the distal tip of the guide wire 10.

The relatively high concentration of tungsten tends to reduce the tensile strength of the plastic jacket 32. To compensate for this reduced strength, it is contemplated that the second outer jacket layer 34, which preferably is formed from PEBAX having little or no radiopaque agent therein, is provided over the first plastic jacket 32. In this configuration, the combination of the first outer jacket layer 32 and the second outer jacket layer 34 provides a guide wire 10 that has a highly radiopaque distal tip, and yet retains the desired strength characteristic. The first and second outer jacket layers preferably extend a few millimeters distally of the distal end 14 of core wire 18 to provide a softer, more atraumatic distal tip to the guide wire 10.

Figure 2:
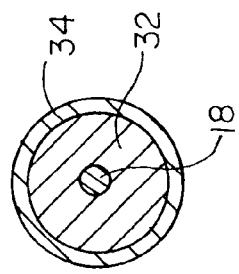
FIG. 2 is a cross-sectional view of the embodiment of FIG. 1 taken along line 2—2.

The first outer jacket layer 32 may have a wall thickness in the range of about 0.002 to 0.008 inch, and the second outer jacket layer 34 may have a wall thickness in the range of about 0.001 to 0.002 inch. FIG. 2 shows a cross-section of the first outer jacket layer 32, the second outer jacket layer 34, and the core wire 18 taken along line 2—2 of FIG. 1.

In another illustrative embodiment, the first outer jacket layer 32, which is disposed between the elongated core and the second outer jacket layer 34, is formed from a bonding material that is particularly suited for forming a bond between the second outer jacket layer 34 and the elongated core wire 18. It is contemplated that the bonding layer may be co-extruded with the second outer jacket layer 34. This provides an efficient method for bonding a plastic jacket 34 to an elongated core wire 18, and in particular a metallic elongated core, without having to apply an adhesive or the like to the elongated core wire 18 by conventional means such as dipping or spraying. Preferably, the bonding material is PLEXAR® available from Quantum Chemical Corporation located in Cincinnati Ohio, BYNEL®, EVA (Ethylene Vinyl Acetate), Urethane, maleic anhydride or a similar material of a category of extrudable adhesives used in extrusion and, in particular, those referred to as tie layers.

Figure 3:
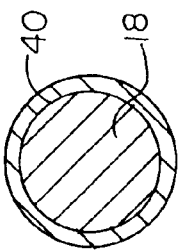
FIG. 3 is a cross-sectional view of the embodiment of FIG. 1 taken along line 3—3.

A TEFLON® sleeve 40 may be provided over the core wire 18 proximal to the first and second outer jacket layers, as shown. The Teflon® sleeve 40 is preferably heat shrunk to the outer surface of the core wire 18 to provide a relatively lubricious surface thereto. FIG. 3 shows the Teflon® sleeve 40 placed around the proximal portion 22 of core wire 18.

It is also contemplated that a number of outer jacket layers may be co-extruded over a mandrel or the like to produce a multi-layer tip assembly having a lumen. In one embodiment, the distal end of a guide wire is positioned in the lumen and the tip assembly is heated. By selecting the appropriate materials, the multi-layer tip assembly may shrink as a result of the heating process, securing the tip to the distal end of the guide wire. In another embodiment, a bonding adhesive may be used, wherein the bonding adhesive may be pressure activated or heat activated. Thus, the tip assembly may be secured to the distal tip of the guide wire by simply applying pressure or heat as appropriate.

FIG. 4 is a cross-sectional side view of another embodiment of the present invention. In this embodiment, a number of outer jacket layers are co-extruded over the entire length of a core wire 50. Although the outer jacket layers are shown extending the entire length of the core wire 50, it is contemplated that the outer jacket layers may be provided only over selected sections of the core wire 50.

In the illustrative embodiment, a bonding layer 52 is co-extruded with any number of layers including an inner plastic jacket layer 54 and an outer plastic jacket layer 56. As noted above, the inner plastic jacket layer 54 may, for example, have a first concentration of a radiopaque agent, and the outer plastic jacket layer 56 may have a second concentration of a radiopaque agent. The bonding layer may form a bond between the elongated core 50 and the inner plastic jacket layer 52. The inner and outer plastic jacket layers 54 and 56 are preferably formed from similar materials so that a bond is formed therebetween during the co-extrusion process.

It is contemplated a lubricious layer may also be co-extruded with the bonding layer, the inner plastic jacket and the outer plastic jacket to provide a lubricious outer surface thereto. The lubricious layer may be a hydrophilic coating such as Union Carbide POLYSLIP® P106 and T503M, or a coating similar to that described in U.S. Pat. No. 5,702,754 to Zong. Some thermoplastic urethane materials may provide a hydrophilic coating that is extrudable. Alternatively, the lubricious layer may be applied by dipping or spraying, as is known in the art.

An advantage of using a hydrophilic coating is that the guide wire and/or guide wire tip may be used to deliver drugs or the like to the treated vessel. Hydrophilic coatings are effective for absorbing liquids, including liquid drugs. When the hydrophilic coating absorbed a drug, such as heparin for example, and later comes into contact with a vessel wall or the like, some of the absorbed drug is delivered to the vessel wall. Thus, it is contemplated that the hydrophilic coating may be a drug coating.

FIG. 5 is a cross-sectional view of the embodiment of FIG. 4 taken along line 5—5 showing a bonding layer 52 that is co-extruded with an inner plastic jacket layer 54 and an outer plastic jacket layer 56 over core wire 50. In the illustrative embodiment, the bonding layer 52 and the outer plastic jacket layer 56 are thinner than the inner plastic jacket layer 54. When the inner plastic jacket layer 54 is loaded with a high concentration of a radiopaque agent, this configuration may provide the maximum radiopacity to the distal tip of the guide wire, while maintaining the other desired characteristics of the guide wire.

FIG. 6 is a partial cross-sectional side view of a distal portion of yet another embodiment of the present invention. In this illustrative embodiment, a bonding layer 70, an inner plastic jacket layer 72, an outer plastic jacket layer 74 and a lubricious layer 76 are all co-extruded over a core wire 80. The bonding layer 70 preferably forms a bond between the elongated core wire 80 and the inner plastic jacket layer 72. The inner and outer plastic jacket layers 72 and 74 are preferably formed from similar materials so that a bond is formed therebetween during the co-extrusion process. The lubricious layer may be an extrudable hydrophilic coating that bonds to the outer plastic jacket 74.

FIG. 7 is a cross-sectional view of the embodiment of FIG. 6 taken along line 7—7. In the illustrative embodiment, the bonding layer 70 and the outer plastic jacket layer 74 are thinner than the inner plastic jacket layer 72. When the inner plastic jacket layer 72 is loaded with a relatively high concentration of a radiopaque agent, for example, this configuration may provide the maximum radiopacity to the distal tip of the guide wire, while maintaining the other desired characteristics of the guide wire.

It is intended that the foregoing detailed description be regarded as illustrative rather than limiting and that it is understood that the following claims including all equivalents are intended to define the scope of the invention.

What is claimed is:

1. A method for making a guide wire comprising the steps of:
   providing an elongated core wire having a tapered portion with an outer axial surface; and
   co-extruding at least two plastic jacket layers and a bonding layer over at least a portion of said outer axial surface;
   co-extruding the bonding layer, the inner plastic jacket and the outer plastic jacket beyond a distal end of the elongated core wire to form an atraumatic tip, the atraumatic tip having a length and a width, the length being greater than the width; and
   wherein a first jacket layer is disposed closer to said elongated core wire than a second jacket layer, said first jacket layer is thicker than said second jacket layer, said first jacket layer contains a concentration of a radiopaque agent, and said second jacket layer contains substantially no radiopaque agent, said first jacket layer and said second jacket layer forming a bond therebetween during said co-extruding step.

2. A method for making a guide wire comprising the steps of:
   providing an elongated core wire having a tapered portion with an outer axial surface; and
   co-extruding at least two plastic jacket layers and a bonding layer over at least a portion of said outer axial surface;
   co-extruding the bonding layer, the inner plastic jacket and the outer plastic jacket beyond a distal end of the elongated core wire to form an atraumatic tip, the atraumatic tip having a length and a width, the length being greater than the width; and wherein said at least two plastic jacket layers collectively have a wall thickness and wherein one of said at least two plastic jacket layers comprises a majority of said wall thickness and contains a radiopaque agent, said at least two plastic jacket layers forming bonds therebetween during said co-extruding step.

3. A method according to claim 1, wherein the concentration of said radiopaque agent in said first jacket layer is at least about 50 percent by weight.

4. A method according to claim 1, wherein said radiopaque agent is selected from the group consisting of tungsten, tantalum, platinum, and gold.

5. A method for making a guide wire comprising the steps of:
   providing an elongated core wire having a tapered portion with an outer axial surface; and
   co-extruding a bonding layer, an inner plastic jacket and an outer plastic jacket over at least a portion of said outer axial surface;
   co-extruding the bonding layer, the inner plastic jacket and the outer plastic jacket beyond a distal end of the elongated core wire to form an atraumatic tip, the atraumatic tip having a length and a width, the length being greater than the width; and
   wherein said inner plastic jacket contains a first concentration of a radiopaque agent and said outer plastic jacket contains a second concentration of said radiopaque agent, wherein said first concentration is greater than said second concentration, said bonding layer forming a bond between said elongated core wire and said inner plastic jacket, said inner plastic jacket and said outer plastic jacket forming a bond therebetween during said co-extruding step.

6. A method according to claim 5, wherein a lubricious layer is co-extruded along with said bonding layer, said inner plastic jacket, and said outer plastic jacket, said lubricious layer and said outer plastic jacket forming a bond therebetween during said co-extruding step.

7. A method according to claim 5, wherein said first concentration is at least about 50 percent by weight.

* * * * *